(12) United States Patent
Donnadieu et al.

(10) Patent No.: US 6,358,938 B1
(45) Date of Patent: Mar. 19, 2002

(54) SYNERGISTIC FUNGICIDAL COMPOSITION

(75) Inventors: Joëlle Donnadieu, Sainte Foy les Lyon; Patrice Duvert, Lyons; Richard Mercer, Ecully, all of (FR)

(73) Assignee: Rhone-Poulenc Agro, Lyon Cedex (FR)

( * ) Notice: Subject to any disclaimer, the term of this patent is extended or adjusted under 35 U.S.C. 154(b) by 0 days.

(21) Appl. No.: 09/402,218

(22) PCT Filed: Apr. 1, 1998

(86) PCT No.: PCT/FR98/00654
§ 371 Date: Feb. 15, 2000
§ 102(e) Date: Feb. 15, 2000

(87) PCT Pub. No.: WO98/44801
PCT Pub. Date: Oct. 15, 1998

(30) Foreign Application Priority Data

Apr. 4, 1997 (FR) ............................. 97 04369

(51) Int. Cl.$^7$ ........................ A01N 57/18; A01N 47/10; A01N 59/26
(52) U.S. Cl. ....................... 514/141; 424/601; 424/602; 424/605; 424/606; 514/478; 514/479
(58) Field of Search ................................. 514/141, 478, 514/479; 424/601, 602, 605, 606

(56) References Cited

PUBLICATIONS

Tammes, "Isoboles, a graphic representation of synergism in pesticides", *Netherlands Journal of Plant Pathology*, 70 (1964), pp. 73–80.

*The Pesticide Manual*, 10$^{th}$ edition, ed. Clive Tomlin, The British Crop Protection Council, London, pp. 530–532, 843–845 (1994).

Couch et al, "Synergistic and antagonistic interactions of fungicides against *Pythium aphanidermatum* on perennial ryegrass", *Crop Protection*, vol. 10, No. 5 (1991), pp. 386–390, XP002050973.

*Primary Examiner*—Allen J. Robinson
(74) *Attorney, Agent, or Firm*—Burns, Doane, Swecker & Mathis, L.L.P.

(57) ABSTRACT

Synergistic fungicidal composition comprising propamocarb and a derivative of phosphorous acid; and
  process for the curative or preventative control of phytopathogenic fungi by use of such a composition.

36 Claims, No Drawings

SYNERGISTIC FUNGICIDAL COMPOSITION

This application is a 371 of PCT/FR98/80654, filed Apr. 1, 1998.

The subject of the present invention is a synergistic fungicidal composition comprising propamocarb and a derivative of phosphorous acid and a process which makes use of the said composition and which is intended for the curative or preventive protection of crops against fungal attacks.

It is always desirable to improve the spectrum of activity and the effectiveness of such compounds with a fungicidal effect or to reinforce them by combining them with other molecules in order to obtain a more effective product (combination with a systemic fungicide, these fungicides instead being molecules of "contact" type) or alternatively to prevent the appearance of fungal strains which are resistant to these new fungicides.

It is also highly desirable to have available fungicidal products which enjoy an improved persistance of effect, likely to space out in time the number of plant-protection treatments necessary for satisfactory control of the parasites.

It is, in any event, particularly advantageous to be able to decrease the amount of chemicals distributed in the environment, while ensuring high-performance protection of crops against fungal attacks.

It has now been found that one (or a number) of the above objectives could be achieved by virtue of the fungicidal composition according to the present invention.

The subject of the present invention is therefore, in first place, a synergistic fungicidal composition comprising, as compound A, propamocarb, also known as propyl 3-(dimethylamino)propylcarbamate, and at least one fungicidal compound B chosen from the group comprising derivatives of phosphorous acid, for example metal phosphites, such as fosetyl-Al, and phosphorous acid itself and its alkali metal or alkaline earth metal salts.

The fungicidal composition according to the invention advantageously comprises the components A and B in an A/B ratio by weight of between 1/12 and 12/1, is preferably between 1/3 and 3/1, and more advantageously still in a ratio equal to 1.

It is clearly understood that the said fungicidal composition can contain a single compound B or more than one such compound, for example 1, 2 or 3 compounds B, according to the use for which the composition is intended.

Preference is further given, among the more especially preferred meanings of the compound B defined above, to fosetyl-Al. The composition is preferably not applied on lawns. In an entirely unexpected way, the composition according to the invention then significantly improves the effect of the active materials taken separately with respect to a number of fungi which are particularly harmful to crops, for example in particular grapes or the Solanaceae. This improvement is reflected in particular by a decrease in the doses of each of the constituents, which is particularly advantageous for the user and the environment. The fungicidal product thus exhibits synergic properties attested by application of the Tammes method, "Isoboles, a graphic representation of synergism in pesticides", Netherlands Journal of Plant Pathology, 70(1964), pp. 73–80.

Preferably, when the component B is fosetyl-Al, the A/B ratio is between 1/3 and 3/1, and, more advantageously still, this ratio is equal to 1, for all the crops envisaged.

The structures corresponding to the common names of the active materials A and B are shown in at least one of the following 2 works:

"The Pesticide Manual", edited by Clive Tomlin and published by The British Crop Protection Council, 10th edition (pages 843 and 530);

l'Index phytosanitaire [Plant-protection index] 1994, published by l'Association de Coordination Technique Agricole [Agricultural Technical Coordination Association], 30th edition.

The fungicidal composition according to the invention comprises, as active material, a compound A and at least one compound B as a mixture with solid or liquid vehicles which are acceptable in agriculture and/or surface-active agents which are also acceptable in agriculture. In particular, the inert and conventional vehicles and the conventional surface-active agents can be used. These compositions cover not only compositions which are ready to be applied to the crop to be treated by means of a suitable device, such as a spray device, but also commercial concentrated compositions which have to be diluted before application to the crop. The combination of at least one compound A with at least one compound B is denoted as active material.

These compositions can also contain any kind of other ingredients such as, for example, protective colloids, adhesives, thickening agents, thixotropic agents, penetrating agents, stabilizing agents, sequestering agents and the like. More generally, the compounds A and B can be combined with all the solid or liquid additives corresponding to the conventional formulating techniques.

Generally, the compositions according to the invention usually contain from 0.05 to 95% (by weight) of active material, one or more solid or liquid vehicles and, optionally, one or more surface-active agents.

In the present account, the term "vehicle" denotes a natural or synthetic, organic or inorganic material with which the active material is combined to facilitate its application on the aerial parts of the plant. This vehicle is thus generally inert and it must be acceptable in agriculture, especially on the treated plant. The vehicle can be solid (clays, natural or synthetic silicates, silica, resins, waxes, solid fertilizers and the like) or liquid (water, alcohols, especially butanol, and the like).

The surface-active agent can be an emulsifying, dispersing or wetting agent of ionic or nonionic type or a mixture of such surface-active agents. There may be mentioned, for example, salts of polyacrylic acids, salts of lignosulphonic acids, salts of phenolsulphonic or naphthalenesulphonic acids, polycondensates of ethylene oxide with fatty alcohols or with fatty acids or with fatty amines, substituted phenols, (especially alkylphenols or arylphenols), salts of esters of sulphosuccinic acids, taurine derivatives (especially alkyltaurates), phosphoric esters of polyoxyethylenated phenols or alcohols, esters of fatty acids and of polyols, and the derivatives of the above compounds containing sulphate, sulphonate and phosphate functional groups. The presence of at least one surface-active agent is generally indispensable when the active material and/or the inert vehicle is/are not soluble in water and the carrier agent for application is water.

The compositions for agricultural use according to the invention can thus contain the active material within very wide limits, ranging from 0.05% to 95% (by weight). Their surface-active agent content is advantageously between 5% and 40% by weight. Except when otherwise indicated, the percentages given in this description, including the claims, are by weight.

These compositions according to the invention are themselves in fairly diverse, solid or liquid forms.

There may be mentioned, as forms of solid compositions, the powders for dusting (with an active material content which can range up to 100%) and the granules, especially those obtained by extrusion, by compacting, by impregnation of a granulated support, or by granulation from a powder (the active material content in these granules being between 0.5 and 80% for the latter cases), the tablets or effervescent tablets.

The fungicidal composition according to the invention can also be used in the form of powders for dusting; it is also possible to use a composition comprising 50 g of active material and 950 g of talc; it is also possible to use a composition comprising 20 g of active material, 10 g of finely divided silica and 970 g of talc; these constituents are mixed and milled and the mixture is applied by dusting.

There may be mentioned, as forms of liquid compositions or those intended to constitute liquid compositions at the time of application, solutions, in particular water-soluble concentrates, emulsions, suspension concentrates, aerosols, wettable powders (or powder to be sprayed), pastes or gels.

The suspension concentrates, which can be applied by spraying, are prepared so as to obtain a stable fluid product which does not settle out and they generally contain from 10 to 75% of active material, from 0.5 to 15% of surface-active agents, from 0.1 to 10% of thixotropic agents and from 0 to 10% of suitable additives, such as antifoaming agents, corrosion inhibitors, stabilizing agents, penetrating agents and adhesives and, as vehicle, water or an organic liquid in which the active material is insoluble or nearly insoluble: certain organic solid materials or inorganic salts can be dissolved in the vehicle to aid in preventing sedimentation or as antigels for water.

A suspension concentrate composition is given here as an example:

SC EXAMPLE 1

| | |
|---|---|
| active material | 500 g |
| polyethoxylated tristyrylphenyl phosphate | 50 g |
| polyethoxylated alkylphenol | 50 g |
| sodium polycarboxylate | 20 g |
| ethylene glycol | 50 g |
| organopolysiloxane oil (antifoaming agent) | 1 g |
| polysaccharide | 1.5 g |
| water | 316.5 g | wettable powders (or powder to be sprayed) are generally prepared so that they contain 20 to 95% of active material, and they generally contain, in addition to the solid vehicle, from 0 to 30% of a wetting agent, from 3 to 20% of a dispersing agent and, when this is necessary, from 0.1 to 10% of one or more stabilizing agents and/or other additives, such as penetrating agents, adhesives, or anticlumping agents, dyes, and the like.

To obtain powders to be sprayed or wettable powders, the active materials are intimately mixed, in suitable mixers, with the additional substances and the mixture is milled with mills or other suitable grinders. Powders to be sprayed are thereby obtained with advantageous wettability and suspensibility; they can be suspended in water at any desired concentration and these suspensions can be used very advantageously in particular for application to plant leaves.

Pastes can be produced in place of wettable powders. The conditions and modes of production and use of these pastes are similar to those of wettable powders or powders to be sprayed.

Various wettable powder (or powder to be sprayed) compositions are given here as examples:

WP EXAMPLE 1

| | |
|---|---|
| active material | 50% |
| ethoxylated fatty alcohol (wetting agent) | 2.5% |
| ethoxylated phenylethylphenol (dispersing agent) | 5% |
| chalk (inert vehicle) | 42.5% |

WP EXAMPLE 2

| | |
|---|---|
| active material | 10% |
| C13 branched-type synthetic oxo alcohol, ethoxylated with 8 to 10 molecules of ethylene oxide (wetting agent) | 0.75% |
| neutral calcium lignosulphonate (dispersing agent) | 12% |
| | 12% |
| calcium carbonate (inert filler) | qs for 100% |

WP EXAMPLE 3

This wettable powder contains the same ingredients as in the above example, in the proportions below:

| | |
|---|---|
| active material | 75% |
| wetting agent | 1.50% |
| dispersing agent | 8% |
| calcium carbonate (inert filler) | qs for 100% |

WP EXAMPLE 4

| | |
|---|---|
| active material | 90% |
| ethoxylated fatty alcohol (wetting agent) | 4% |
| ethoxylated phenylethylphenol (dispersing agent) | 6% |

WP EXAMPLE 5

| | |
|---|---|
| active material | 50% |
| mixture of anionic and nonionic surface-active agents (wetting agent) | 2.5% |
| sodium lignosulphonate (dispersing agent) | 5% |
| kaolin clay (inert vehicle) | 42.5% |

Aqueous dispersions and emulsions, for example the compositions obtained by diluting a wettable powder or an emulsifiable concentrate according to the invention with water, are contained within the general scope of the present invention. Emulsions can be of the water-in-oil or oil-in-water type and they can have a thick consistency, like that of a "mayonnaise".

The fungicidal compositions according to the invention can be formulated in the form of water-dispersible granules, which also come within the scope of the invention.

These dispersible granules, with a bulk density generally of between approximately 0.3 and 0.6, have a particle size generally of between approximately 150 and 2000 and preferably between 300 and 1500 microns.

The active material content of these granules is generally between approximately 1% and 90%, and preferably between 25% and 90%.

The rest of the granule is essentially composed of a solid filler and, optionally, of surface-active adjuvants which confer water-dispersibility properties on the granule. These granules can be essentially of two distinct types according to whether the filler held is soluble or insoluble in water. When the filler is water-soluble, it: can be inorganic or, preferably, organic. Excellent results were obtained with urea. In the case of an insoluble filler, the latter is preferably inorganic, such as, for example, kaolin or bentonite. It is then advantageously accompanied by surface-active agents (in a proportion of 2 to 20% by weight of the granule) of which more than half consists of, for example, at least one dispersing agent, essentially anionic, such as an alkali metal or alkaline earth metal polynaphthalenesulphonate or an alkali metal or alkaline earth metal lignosulphonate, the remainder consisting of nonionic or anionic wetting agents such as an alkali metal or alkaline earth metal alkylnaphthalenesulphonate.

Moreover, although this is not indispensable, it is possible to add other adjuvants such as antifoaming agents.

The granule according to the invention can be prepared by mixing the necessary ingredients and then granulating according to several techniques known per se (granulator, fluid bed, sprayer, extrusion, and the like). The preparation generally finishes with a crushing followed by a sieving to the particle size chosen within the limits mentioned above. Granules obtained as above and then impregnated with a composition containing the active material can alternatively be used.

It is preferably obtained by extrusion, by carrying out the preparation as indicated in the examples below.

DG EXAMPLE 1

Dispersible granules

90% by weight of active material and 10% of urea in the form of pearls are mixed in a mixer. The mixture is then milled in a pin mill. A powder is obtained which is moistened with approximately 8% by weight of water. The moist powder is extruded in a perforated-roller extruder. A granular material is obtained which is dried, and then crushed and sieved, so as to respectively keep only the granules with a size of between 150 and 2000 microns.

DG EXAMPLE 2

Dispersible granules

The following constituents are mixed in a mixer:

| | |
|---|---|
| active material | 75% |
| wetting agent (sodium alkylnaphthalene-sulphonate) | 2% |
| dispersing agent (sodium polynaphthalene-sulphonate) | 8% |
| water-insoluble inert filler (kaolin) | 15% |

This mixture is granulated on a fluid bed in the presence of water and then dried, crushed and sieved so as to obtain granules with a size of between 0.15 and 0.80 mm.

These granules can be used alone or in solution or dispersion in water so as to obtain the required dose. They can also be used to prepare combinations with other active materials, especially fungicides, the latter being in the form of wettable powders or granules or aqueous suspensions.

As regards the compositions which are suitable for storage and transportation, they more advantageously contain from 0.5 to 95% (by weight) of active material.

Another subject of the invention is a process for the curative or preventive control of fungi which are phytopathogenic towards crops, characterized in that an effective and non-phytotoxic amount of a combination of the compound A and at least one compound B, for example in a fungicidal composition according to the invention, is applied on the aerial parts of plants or on the ground.

The fungi which are phytopathogenic towards crops which can be combatted by this process are in particular those:

from the Oomycetes group:
from the Phytophthora genus, such as *Phytophthora phaseoli, Phytophthora citrophthora, Phytophthora capsici, Phytophthora cactorum, Phytophthora palmivora, Phytophthora cinnamoni, Phytophthora megasperma, Phytophthora parasitica, Phytophthora fragariae, Phytophthora cryptogea, Phytophthora porri, Phytophthora nicotianae* or *Phytophthora infestans;*
from the Peronosporaceae family, in particular *Plasmopara viticola* (grape downy mildew), *Plasmopara halstedei* (sunflower downy mildew), Pseudoperonospora sp (in particular downy mildew of cucurbits (*Pseudoperonospora cubensis*) and of hops (*Pseudoperonospora humili*)), *Bremia lactucae* (lettuce downy mildew), *Peronospora tabacinae* (tobacco downy mildew), *Peronospora destructor* (downy mildew of crucifers), *Peronospora parasitica* (downy-mildew of cabbage) or *Peronospora farinosa* (downy mildew of endives and downy mildew of beet).

The crops envisaged in the context of the present invention are preferably vegetable crops (bean, onion, cucurbits, cabbage, potato, tomato, capsicum, spinach, pea, lettuce or endives), fruit crops (strawberry plants or raspberry bushes), arboricultural crops (apple trees, pear trees, ginseng, lemon trees, coconut palms, cacao trees, heveas or banana trees), the vine, sunflower, beet, tobacco and ornamental plants.

The fungicidal composition which is the subject of the invention is applied by means of various treatment processes, such as:

spraying a liquid comprising the said composition on the aerial parts of the crops to be treated, dusting, the incorporation of granules or of powders into the soil, sprinkling, injecting into trees or painting.

The spraying of a liquid on the aerial parts of the crops to be treated is the preferred treatment process.

"Effective and non-phytotoxic amount" is understood to mean an amount of composition according to the invention which is sufficient to make possible control or destruction of the fungi present or capable of appearing on the crops and which does not result in any significant phytotoxicity symptom with respect to the said crops. Such an amount is capable of varying within wide limits depending on the fungus to be controlled, the type of crop, the weather conditions and the compounds included in the fungicidal composition according to the invention. This amount can be determined by systematic tests in the field, within the scope of the person skilled in the art.

The use doses during the implementation of the process according to the invention will then generally be, on the vine, vegetable crops, arboriculture, citrus fruits and the like:

by leaf treatment:

500 to 6000 g/ha of compound B, e.g. fosetyl-Al,+500 to 6000 g/ha of compound A and more specifically 1000 to 3000 g/ha+1000 to 3000 g/ha, i.e. a total dose of composition according to the invention of between 1000 and 12,000 g/ha, preferably between 2000 and 6000 g/ha. Use is preferably made of a total dose of composition according to the invention equal to 3000 g/ha, i.e. 1500 g/ha of compound A+1500 g/ha of compound B.

By soil treatment (sprinkling):

25 to 300 kg/ha of compound B, e.g. fosetyl-Al,+25 to 300 kg/ha of compound A and more specifically 50 to 150 kg/ha+50 to 150 kg/ha, i.e. a total dose of composition according to the invention of between 50 and 600 kg/ha, preferably between 100 and 300 kg/ha. Use is preferably made of a total dose of composition according to the invention equal to 200 kg/ha, i.e. 100 kg/ha of compound A+100 kg/ha of compound B.

The following examples are given purely by way of illustration of the invention, which they do not limit in any way.

EXAMPLE 1

Test on the vine

The fungicides experimented on are as follows:

Aliette WP: WP formulation containing 80% of fosetyl-Al/kg,

Previcur N: SL formulation containing 722 g of propamocarb/l.

The fungicidal compositions experimented on are as follows:

Aliette at active material (a.m.) doses of 62, 125, 250, 500, 1000, 2000 and 4000 ppm.

Previcur N at a.m. doses of 62, 125, 250, 500, 1000, 2000 and 4000 ppm.

Aliette+Previcur at a.m. doses of 125+62, 250+125, 500+250, 1000+500, 2000+1000 and 4000+2000 ppm (ratio 2/1).

Aliette+Previcur at a.m. doses of 125+125, 250+250, 500+500, 1000+1000, 2000+2000 and 4000+4000 ppm (ratio 1/1).

Vine seedlings (Chardonnay var.) aged 8 weeks are treated with the fungicidal compositions at the abovementioned doses (3 repetitions/dose). One day after the treatment, the seedlings are infected with an aqueous suspension containing 100,000 spores of *Plasmopara viticola*/ml of inoculum. The seedlings are then placed in a controlled-environment chamber at 20° C., 100% RH (relative humidity) for 9 days. An assessment is then carried out. This consists in estimating the proportion of sick seedlings for each test factor and, by comparison with an untreated/infected control, in defining the percentage of effectiveness according to the following formula: % practical effectiveness=100×(% Control infection−% Test infection)/% Control infection. The theoretical effectiveness according to the Colby formula is calculated from the following formula: % A+B theoretical effectiveness=% A practical eff.+% B practical eff.−(% A practical eff.×% B practical eff./100).

Practical effectiveness (observed):

| | | Previcur (ppm) | | | | | | |
|---|---|---|---|---|---|---|---|---|
| | | 0 | 62 | 125 | 250 | 500 | 1000 | 2000 | 4000 |
| | | Practical effectiveness (observed): | | | | | | | |
| Aliette (ppm) | 0 | | 0 | 0 | 12 | 5 | 12 | 21 | 39 |
| | 62 | 0 | | | | | | | |
| | 125 | 0 | 0 | 0 | | | | | |
| | 250 | 9 | | 12 | 4 | | | | |
| | 500 | 18 | | | 21 | 29 | | | |
| | 1000 | 54 | | | | 54 | 70 | | |
| | 2000 | 68 | | | | | 79 | 100 | |
| | 4000 | 91 | | | | | | 96 | 10 |
| | | Theoretical effectiveness (according to Colby) | | | | | | | |
| Aliette (ppm) | 0 | | 0 | 0 | 12 | 5 | 12 | 21 | 39 |
| | 62 | 0 | | | | | | | |
| | 125 | 0 | 0 | 0 | | | | | |
| | 250 | 9 | | 9 | 20 | | | | |
| | 500 | 18 | | | 28 | 22 | | | |
| | 1000 | 54 | | | | 56 | 60 | | |
| | 2000 | 68 | | | | | 72 | 75 | |
| | 4000 | 91 | | | | | | 93 | 95 |
| | | Synergy values: | | | | | | | |
| Aliette (ppm) | 0 | | 0 | 0 | 12 | 5 | 12 | 21 | 39 |
| | 62 | 0 | | | | | | | |
| | 125 | 0 | 0 | 0 | | | | | |
| | 250 | 9 | | +3 | −16 | | | | |
| | 500 | 18 | | | −7 | +7 | | | |
| | 1000 | 54 | | | | −2 | +10 | | |
| | 2000 | 68 | | | | | +7 | +25 | |
| | 4000 | 91 | | | | | | +3 | +5 |

A good synergistic relationship is recorded.

EXAMPLE 2

Test on cabbage

The fungicides experimented on are as follows:

Aliette WP: WP formulation containing 80% of fosetyl-Al/kg

Previcur N: SL formulation containing 722 g of propamocarb/l.

The fungicidal compositions experimented on are as follows:

Aliette at active material (a.m.) doses of 125, 250, 500, 1000, 2000, 4000 and 8000 ppm.

Previcur N at a.m. doses of 125, 250, 500, 1000 and 2000 ppm.

Aliette+Previcur at a.m. doses of 500+125, 1000+250, 2000+500, 4000+1000 and 8000+20C0 ppm (ratio 4/1).

Aliette+Previcur at a.m. doses of 250+125, 500+250, 1000+500, 2000+1000 and 4000+2000 ppm (ratio 2/1).

Aliette+Previcur at a.m. doses of 125+125, 250+250, 500+500, 1000+1000 and 2000+2000 ppm (ratio 1/1).

Cabbage seedlings (Cabus de Brunswick var.) aged 10 days are treated with the fungicidal compositions at the abovementioned doses (3 repetitions/dose). One day after the treatment, the seedlings are infected with an aqueous suspension containing 50,000 spores of *Peronospora parasitica*/ml of inoculum. The seedlings are then placed in a controlled-environment chamber at 15° C., 100% RH (relative humidity) for 6 days.

An assessment is then carried out. This consists in estimating the proportion of sick seedlings for each test factor and, by comparison with an untreated/infected control, in defining the percentage of effectiveness according to the following formula: % practical effectiveness=100×(% Control infection−% Test infection)/% Control infection. The theoretical effectiveness according to the Colby formula is calculated from the following formula: % A+B theoretical effectiveness=% A practical eff.+% B practical eff.−(% A practical eff.×% B practical eff./100).

|  |  | Previcur (ppm) | | | | |
|---|---|---|---|---|---|---|
|  |  | 0 | 125 | 250 | 500 | 1000 | 2000 |
| Practical effectiveness (observed): | | | | | | | |
| Aliette | 0 |  | 0 | 7 | 17 | 73 | 94 |
| (ppm) | 125 | 0 | 0 | | | | |
|  | 250 | 0 | 0 | 60 | | | |
|  | 500 | 0 | 3 | 20 | 87 | | |
|  | 1000 | 0 |  | 53 | 73 | 97 | |
|  | 2000 | 20 |  |  | 87 | 95 | 100 |
|  | 4000 | 47 |  |  |  | 98 | 99 |
|  | 8000 | 83 |  |  |  |  | 100 |
| Theoretical effectiveness (according to Colby) | | | | | | | |
| Aliette | 0 |  | 0 | 7 | 17 | 73 | 94 |
| (ppm) | 125 | 0 | 0 | | | | |
|  | 250 | 0 | 0 | 7 | | | |
|  | 500 | 0 | 0 | 7 | 17 | | |
|  | 1000 | 0 |  | 7 | 17 | 73 | |
|  | 2000 | 20 |  |  | 34 | 78 | 95 |
|  | 4000 | 47 |  |  |  | 89 | 97 |
|  | 8000 | 83 |  |  |  |  | 99 |
| Synergy values: | | | | | | | |
| Aliette | 0 |  | 0 | 7 | 17 | 73 | 94 |
| (ppm) | 125 | 0 | 0 | | | | |
|  | 250 | 0 | 0 | +53 | | | |
|  | 500 | 0 | +3 | +13 | +70 | | |
|  | 1000 | 0 |  | +46 | +56 | +24 | |
|  | 2000 | 20 |  |  | +53 | +17 | +5 |
|  | 4000 | 47 |  |  |  | +12 | +2 |
|  | 8000 | 83 |  |  |  |  | +1 |

A good synergistic relationship is recorded.

EXAMPLE 3

Test on potato

The fungicides experimented on are as follows:
Aliette WP: WP formulation containing 80% of fosetyl-Al/kg
Previcur N: SL formulation containing 722 g of propamocarb/l.

The fungicidal compositions experimented on are as follows:
Aliette at active material (a.m.) doses of 500, 1000, 2000, 4000 and 8000 ppm.
Previcur N at a.m. doses of 62, 125, 250, 500, 1000, 2000 and 4000 ppm.
Aliette +Previcur at a.m. doses of 500+125, 1000+250, 2000+500, 4000+1000 and 8000+2000 ppm (ratio 4/1).
Aliette+Previcur at a.m. doses of 500+250, 1000+500, 2000+1000, 4000+2000 and 8000+4000 ppm (ratio 2/1).
Aliette+Previcur at a.m. doses of 500+500, 1000+1000, 2000+2000 and 4000+4000 ppm (ratio 1/1).

Potato seedlings (Bicntge var.) aged 3 weeks are treated with the fungicidal compositions at the abovementioned doses (2 repetitions/dose). One day after the treatment, the seedlings are infected with an aqueous suspension containing 30,000 spores of *Phytophtora infestans* (strain F4.95)/ml of inoculum. The seedlings are then placed in a controlled-environment chamber at 10° C., 100% RH (relative humidity) for 5 days. They are then transferred to 15° C. for an additional 4 days and are finally placed in a greenhouse at 20° C., 100% RH for 2 days more.

An assessment is then carried out. This consists in estimating the proportion of sick seedlings for each test factor and, by comparison with an untreated/infected control, in defining the percentage of effectiveness according to the following formula: % practical effectiveness=100×(% Control infection−Test infection )/% Control infection. The theoretical effectiveness according to the Colby formula is calculated from th e following formula: % A+B theoretical effectiveness=% A practical eff.+% B practical eff.−(% A practical eff.×% B practical eff./100).

Results

|  |  | Previcur (ppm) | | | | | | |
|---|---|---|---|---|---|---|---|---|
|  |  | 0 | 62 | 125 | 250 | 500 | 1000 | 2000 | 4000 |
| Practical effectiveness (observed): | | | | | | | | | |
| Aliette | 0 |  | 0 | 0 | 0 | 0 | 20 | 20 | 45 |
| (ppm) | 500 | 0 |  | 10 | 0 | 0 | | | |
|  | 1000 | 0 |  |  | 10 | 0 | 10 | | |
|  | 2000 | 0 |  |  |  | 15 | 5 | 30 | |
|  | 4000 | 0 |  |  |  |  | 15 | 25 | 60 |
|  | 8000 | 15 |  |  |  |  |  | 25 | 40 |
| Theoretical effectiveness (according to Colby) | | | | | | | | | |
| Aliette | 0 |  | 0 | 0 | 0 | 0 | 20 | 20 | 45 |
| (ppm) | 500 | 0 |  | 0 | 0 | 0 | | | |
|  | 1000 | 0 |  |  | 0 | 0 | 20 | | |
|  | 2000 | 0 |  |  |  | 0 | 20 | 20 | |
|  | 4000 | 0 |  |  |  |  | 20 | 20 | 45 |
|  | 8000 | 15 |  |  |  |  |  | 32 | 53 |
| Synergy values: | | | | | | | | | |
| Aliette | 0 |  | 0 | 0 | 0 | 0 | 20 | 20 | 45 |
| (ppm) | 500 | 0 |  | +10 | 0 | 0 | | | |
|  | 1000 | 0 |  |  | +10 | 0 | −10 | | |
|  | 2000 | 0 |  |  |  | +15 | −15 | +10 | |
|  | 4000 | 0 |  |  |  |  | −5 | +5 | +15 |
|  | 8000 | 15 |  |  |  |  |  | +7 | −13 |

A synergistic relationship is recorded.

What is claimed is:

1. A synergistic fungicidal composition comprising, as compound A, propamocarb, and at least one fungicidal compound B selected from the group consisting of fosetyl-Al, metal phosphites, phosphorous acid, alkali metal salts of phosphorous acid, and alkaline earth metal salts of phosphorous acid;
   said composition comprising the components A and B in an A/B ratio by weight of between 2/1 and 4/1.
2. The fungicidal composition of claim 1, wherein compound B is fosetyl-Al.
3. The fungicidal composition of claim 1, wherein the A/B ratio is 2/1.
4. The fungicidal composition of claim 1, wherein the A/B ratio is 4/1.
5. The fungicidal composition of claim 1, wherein said composition further comprises an agriculturally acceptable solid or liquid vehicle.
6. The fungicidal composition of claim 5, wherein said composition further comprises an agriculturally acceptable surface-active agent.
7. The fungicidal composition of claim 1, wherein said composition comprises from about 0.05 to about 95% (by weight) of active material.

8. A process for controlling phytopathogenic fungi in a medium, said process comprising applying to said medium a synergistic fungicidally effective, non-phytotoxic amount of a compound A, propamocarb, and at least one fungicidal compound B selected from the group consisting of fosetyl-Al, metal phosphites, phosphorous acid, alkali metal salts of phosphorous acid, and alkaline earth metal salts of phosphorous acid;

said compounds A and B being applied in an A/B ratio by weight of between 1/12 and 12/1, with the proviso that said medium excludes lawns.

9. The process of claim 8, wherein said compound B is fosetyl-Al.

10. The process of claim 8, wherein the A/B ratio is between 1/3 and 3/1.

11. The process of claim 10, wherein the A/B ratio is equal to 1.

12. The process of claim 8, wherein compounds A and B are applied as a composition.

13. The process of claim 12, wherein said composition further comprises an agriculturally acceptable solid or liquid vehicle.

14. The process of claim 13, wherein said composition further comprises an agriculturally acceptable surface-active agent.

15. The process of claim 12, wherein said composition comprises from about 0.05 to about 95% by weight of active material.

16. The process of claim 8, wherein compounds A and B are applied sequentially.

17. The process of claim 8, wherein compounds A and B are applied simultaneously.

18. A process for the curative or preventative control of fungi which are phytopathogenic towards crops, said process comprising applying to the aerial parts of crops or to the soil in which they grow to control said phytopathogenic fungi, a synergistic fungicidally effective, non-phytotoxic amount of a compound A, propamocarb, and at least one fungicidal compound B selected from the group consisting of fosetyl-Al, metal phosphites, phosphorous acid, alkali metal salts of phosphorous acid, and alkaline earth metal salts of phosphorous acid; said compounds A and B being applied in an A/B ratio by weight of between 1/12 and 12/1.

19. The process of claim 18, wherein said compound B is fosetyl-Al.

20. The process of claim 18, wherein the A/B ratio is between 1/3 and 3/1.

21. The process of claim 20, wherein the A/B ratio is equal to 1.

22. The process of claim 18, wherein the fungi to be controlled is *Phytophthora phaseoli, Phytophthora citropthora, Phytophthora capsici, Phytophthora cactorum, Phytophthora palmivora, Phytophthora cinnamoni, Phytophthora megasperma, Phytophthora parasitica, Phytophthora fragariae, Phytophthora cryptogea, Phytophthora porri, Phytophthora nicotinianae, Phytophthora infestans, Plasmopara viticola, Plasmopara halstedei, Pseudoperonospora cubensis, Pseudoperonospora humili, Bremia lactucae, Peronospora tabacinae, Peronospora destructor, Peronospora parasitica,* or *Peronospora farinosa.*

23. The process of claim 18, wherein the crops are selected from the group consisting of beans, onions, cucurbits, cabbage, potatoes, tomatoes, capsicum, spinach, peas, lettuce, endives, strawberries, raspberries, apples, pears, ginseng, lemons, coconuts, cacao, heveas, bananas, vines, sunflowers, beets, tobacco, and ornamental plants.

24. The process of claim 18, wherein a total dose of compounds A and B of between about 50 and about 600 kg/ha is applied to the soil.

25. The process of claim 24, wherein the total dose of compounds A and B is between about 100 and about 300 kg/ha.

26. The process of claim 25, wherein the total dose of compounds A and B is equal to about 200 kg/ha.

27. The process of claim 18, wherein compounds A and B are applied sequentially.

28. The process of claim 18, wherein compounds A and B are applied simultaneously.

29. The process of claim 18, wherein compounds A and B are applied as a composition.

30. The process of claim 29, wherein said composition further comprises an agriculturally acceptable solid or liquid vehicle.

31. The process of claim 30, wherein said composition further comprises an agriculturally acceptable surface-active agent.

32. The process of claim 29, wherein said composition comprises from about 0.05 to about 95% by weight of active material.

33. The process of claim 29, wherein a liquid comprising the fungicidal composition is sprayed on the aerial parts of the crops.

34. The process of claim 18, wherein a total dose of compounds A and B of between about 1000 and about 12,000 g/ha is applied to the leaves.

35. The process of claim 34, wherein the total dose of compounds A and B is between about 2000 and about 6000 g/ha.

36. The process of claim 35, wherein the total dose of compounds A and B is equal to about 3000 g/ha.

* * * * *